United States Patent [19]
Cosme

[11] Patent Number: 5,899,886
[45] Date of Patent: * May 4, 1999

[54] PUNCTURE SAFE NEEDLE ASSEMBLY

[76] Inventor: Edgar Z. Cosme, 1626 Peacock La., Fullerton, Calif. 92633

[ * ] Notice: This patent is subject to a terminal disclaimer.

[21] Appl. No.: 08/896,277

[22] Filed: Jul. 7, 1997

[51] Int. Cl.⁶ .................................................. A61M 5/32
[52] U.S. Cl. .......................................... 604/192; 604/263
[58] Field of Search ................................. 604/192, 198, 604/187, 263, 195

[56] References Cited

U.S. PATENT DOCUMENTS 5,643,220  7/1997  Cosme .................................... 604/192

*Primary Examiner*—John D. Yasko
*Attorney, Agent, or Firm*—Maria Erlinda C. Sarno

[57] ABSTRACT

A needle assembly with a needle holder, a needle sleeve movable over the needle holder, and an interlocking member. The needle sleeve encloses a needle holder and is manually extendable and retractable in a telescopic manner to enclose or expose respectively the distal sharp portion of a needle without the aid of a spring or spring-like device. An interlocking member that clamps or slips into the needle holder locks or releases the needle sleeve from the needle holder. In this assembly, the needle is attached to a protruding body to prevent movement of the needle during use. At the proximal end of the needle assembly is a connector for communicating the needle assembly to a hypodermic syringe or other fluid delivery device.

15 Claims, 3 Drawing Sheets

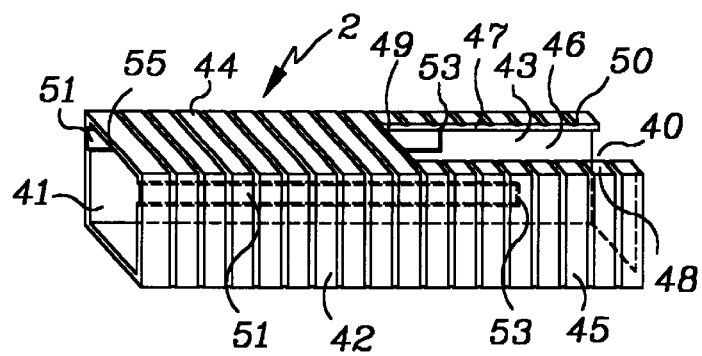
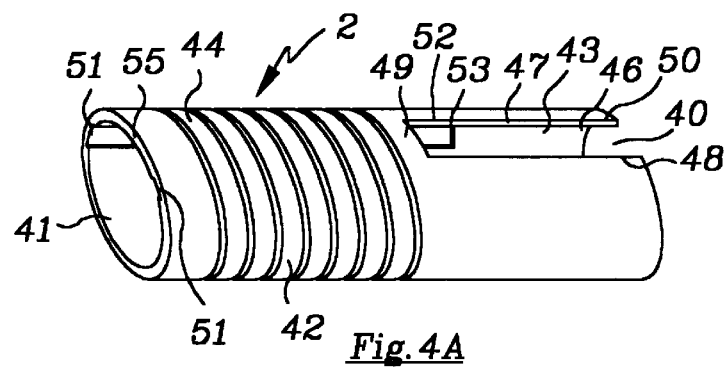
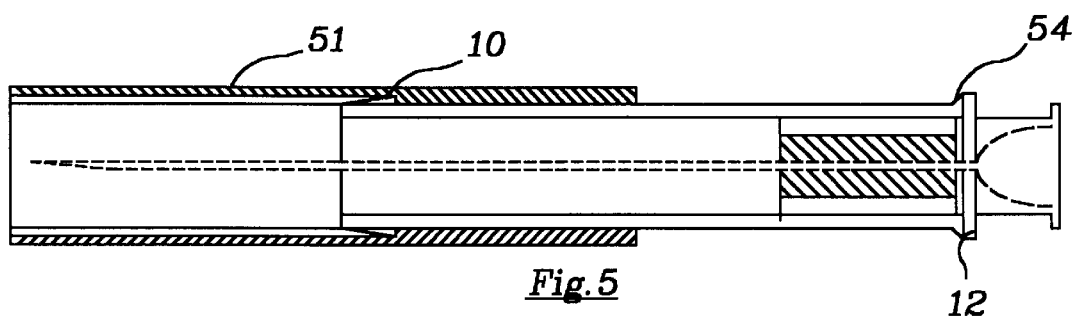
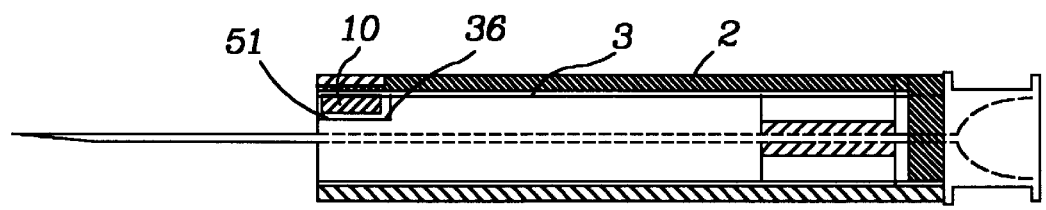
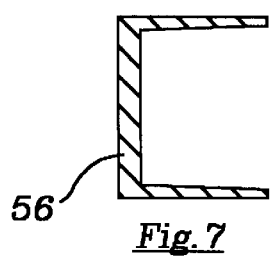

PUNCTURE SAFE NEEDLE ASSEMBLY

BACKGROUND

The present invention relates to a needle assembly with a sliding needle sleeve to shield the sharp distal end of a needle. The needle assembly of this invention is similar to the inventor's previously patented needle assembly, U.S. Pat. 5,643,220. While maintaining the same concept of operation, this invention provides an alternative construction and design. This needle assembly, can be mounted on the forward end of a syringe body or other fluid delivery systems or reservoirs. A syringe utilizing this needle assembly offers protection to the user from unintended, accidental puncture.

It is well known that used syringe needles may cause serious illness or untimely death if a person gets accidentally scratched by a needle previously used on an infected individual. Paramedic and health care personnel in Emergency Room or in an emergency situation are particularly susceptible to receiving a scratch from a contaminated needle dislodged by the thrashing of an accident victim. Further, there has been a growing awareness of the danger of contracting AIDS, hepatitis or other known and unknown viral infections from improperly discarded hypodermic needles.

The needle covers currently used in the medical field employ a conventional needle that is completely shielded by a removable plastic cover. The plastic cover is manually removed before an injection and manually recapped after use. For example, to recap after an injection, the user has to retrieve the needle from the patient before covering the needle with the plastic cover. Consequently, accidental puncture can occur while the user retrieves the needle from a patient before the needle can be covered for protection. Accidental removal of the plastic cover is also possible when a covered needle is discarded which can prick or scratch a user or bystander.

There has been a number of attempts to design a needle cover with varying degrees of success. Most of these devices known in the art, apart from the invention filed by the same inventor, basically consist of two cylindrical components, with one sliding over or inside the other in a telescopic manner aided by a spring mechanism for automatic shielding and exposure of the needle. These needle covers differ in their locking mechanism. These covers are either hard to assemble due to the complexity of the mechanism or are expensive to manufacture.

It is a prime object of the present invention to provide a needle assembly which can protect the sharp tip of the needle from exposure prior to and during the mounting of the needle into the syringe body, between injections and after the needle has been discarded.

It is another object of the present invention to provide a needle assembly that is simple in design, utilizing less plastic material and easy to manufacture.

It is a further object of the invention to provide an inexpensive needle assembly that can be offered as a disposable product.

SUMMARY OF THE INVENTION

The present invention provides another needle assembly that do not utilize a compressible spring device for covering or exposing the sharp distal tip of a needle by a sleeve. This needle assembly includes a needle holder, a needle sleeve and an interlocking member.

The needle holder is shaped like an open trough with a side extension. The trough can be cylindrical, ovoid or rectangular in shape. It has an open lateral distal end and a closed walled proximal end, a walled first and second longitudinal sides, a base and a hollow top surface. On the close walled proximal end is a needle handle, preferably cylindrical in shape, protruding internally inwards of the needle holder, through which a metallic or a sharp polymeric needle is permanently attached. A pair of wing like structure preferably projects from the opposite lateral sides of the cylindrical needle handle to provide greater stability and firmness to the attached needle. The proximal end of the needle, opposite the sharp distal tip is connected through the needle handle into a connector which extends beyond the closed walled proximal end of the needle holder. In one embodiment, there is a recessed cylindrical extension to which an interlocking member can clamp or attach to. The distal end of the needle protrudes from the needle holder. The needle assembly is commonly mounted to a hypodermic syringe but other fluid delivery devices may also be used with this assembly. A protrusion extends radially outward from the outer surface of the longitudinal walls at the distal end of the needle holder. In a cylindrical or similarly shaped needle holder, the protrusion extending radially outward is placed on one or both sides of the cylindrical body towards its distal end. As in the rectangular needle holder, the sides of the cylindrical body from which of these protrusions extend, will be likewise referred to as the longitudinal walls. The protrusion functions both as a stopping and an engagement device between the needle holder and a needle sleeve. The needle sleeve, over and around the needle holder, slides rearward or forward, along the direction of the needle to shield or expose the needle. An interlocking member locks or release the telescopic motion of the needle sleeve relative to the needle holder. Telescopic motion means the needle sleeve can slide rearward or forward over the needle holder from a position wherein the needle sleeve completely envelopes the needle holder to a position where the needle sleeve extends outward away from the needle holder.

BRIEF DESCRIPTION OF THE DRAWINGS

FIG. 4 is a perspective view of a rectangular needle sleeve.

FIG. 4A is a perspective view of a cylindrical needle sleeve.

FIG. 5 is a top view of the needle assembly having no cylindrical extension with the needle shielded by the needle sleeve.

FIG. 6 is a side view of the needle assembly with the needle exposed and the interlocking member clamped to the cylindrical extension of the needle holder.

FIG. 7 is an exploded side view of the capping component.

DETAILED DESCRIPTION OF THE INVENTION

Figure 1:
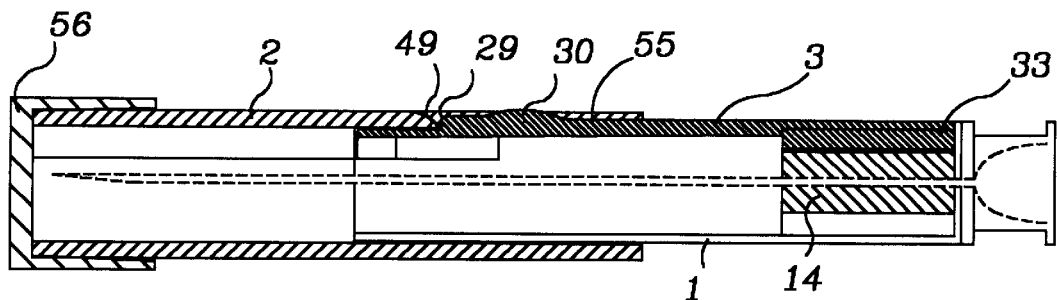
FIG. 1 is a side view of the needle assembly showing the needle holder, the needle sleeve and the interlocking member slipped into the needle holder with the needle covered by the needle sleeve and a cap.
Figure 1A:
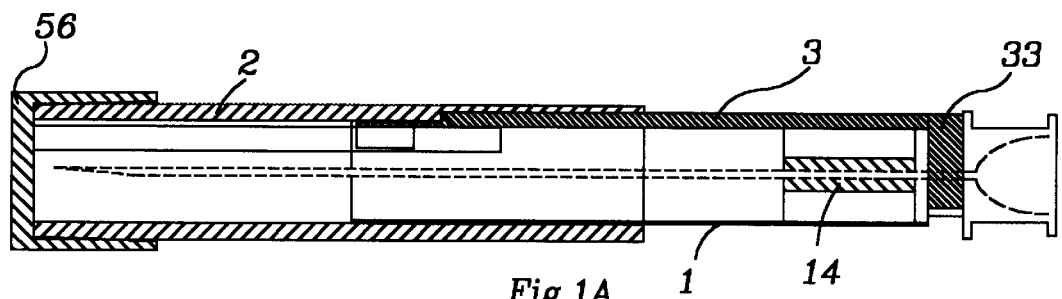
FIG. 1A is a side view of another embodiment of the needle assembly showing the needle holder, the needle sleeve and the interlocking member clamped to a cylindrical extension on the needle holder having the needle covered by the needle sleeve and a cap.

The present invention resides in a needle assembly that do not utilize a compressible spring device for moving or locking a sleeve that covers the sharp distal tip of the needle. This needle assembly includes a needle holder 1, a needle sleeve 2 and an interlocking member 3 as shown in FIGS. 1 and 1A. The needle assembly is commonly mounted into a hypodermic syringe, preferably on a syringe body with a luer lock adapter or on other fluid delivery source or reservoirs used and known in the medical field. In this invention, the distal end is the point away from the operator while the proximal end is the point close to the operator during the use of the device. The outer surface of the needle assembly can be rectangular, cylindrical, ovoid or similarly shaped but is preferably rectangular for ease of handling.

Figure 2:
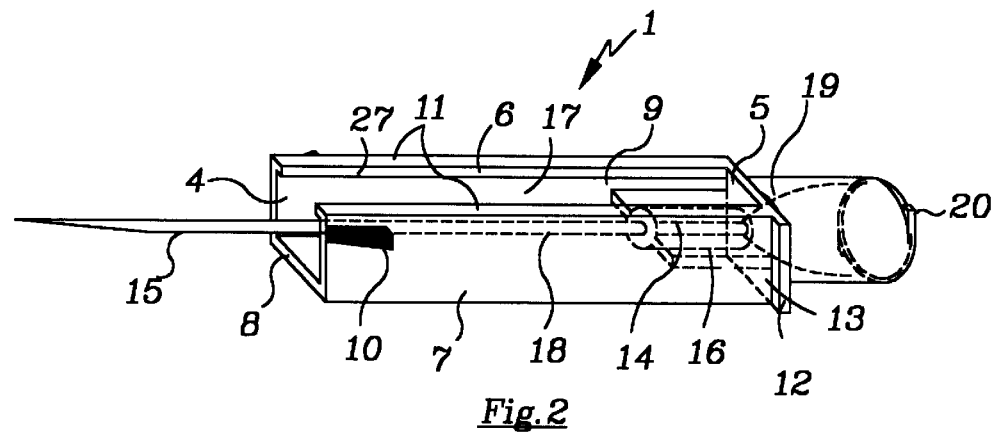
FIG. 2 is a perspective view of a rectangular needle holder showing the wing like structure projecting from the needle handle which is connected to a connector having a luer lock tip, the connector extending from the closed walled proximal end of the needle holder.
Figure 2A:
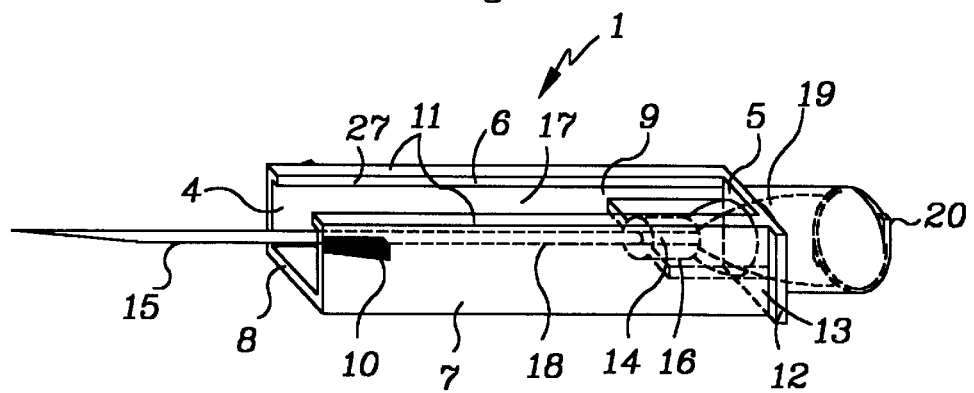
FIG. 2A is a perspective view of a rectangular needle holder showing an alternate design for the wing like structure projecting from the needle handle connected to a connector which extends from inside the closed walled proximal end of the needle holder.
Figure 2B:
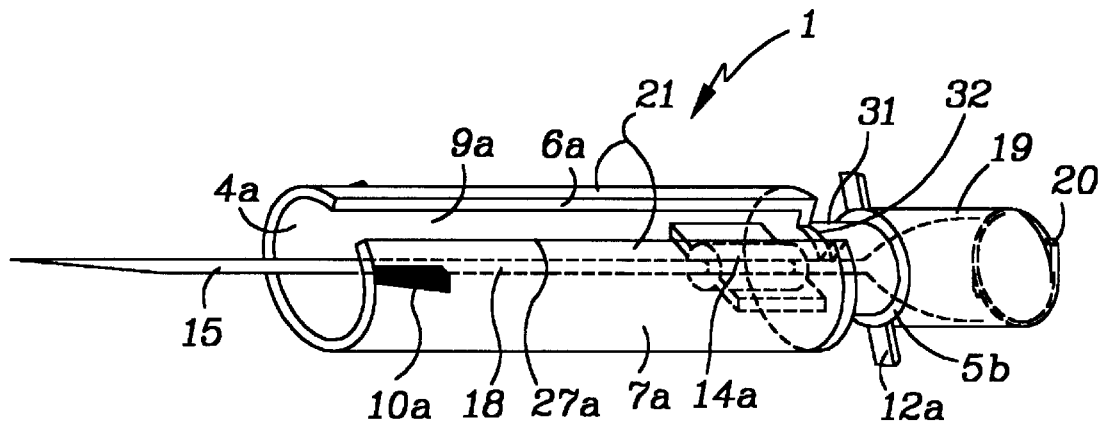
FIG. 2B is a perspective view of a cylindrical needle holder having a recessed cylindrical extension to accommodate a clamping interlocking member.

The main embodiments of the needle holder are shown in FIGS. 2 and 2B. The needle holder is shaped like an open trough with a horizontal extension. Not shown are the ovoid or similarly shaped needle holder. Descriptions for the cylindrical needle holder holds true for the ovoid or similarly shaped needle holder, the only difference between them would be on the contour of their outer surfaces, one would be circular or cylindrical while the other would be oval or ovoid in shape. For the cylindrical and similarly shaped needle holder, the parts corresponding but differentiated from the rectangular needle holder are generally identified with the same number but followed by the small letter a.

The needle holder may be solid, hollow interiored, or a combination of both, made from materials such as glass, metal, hard rubber compound or plastic but is preferably made of plastic polymeric material such as polyvinyl chloride, polyvinylacetate, polyethylene, nylon, polyurethane, polypropylene, polycarbon, polyurethane, ethylene vinyl acetate, polysulfone, combinations of any of these formulations and the like. Hard rubber compound means natural or synthetic rubber compounded with other fillers and agents to give the desired hardness to the resulting rubber material.

One embodiment of the needle holder has an open lateral distal end 4 and a closed walled proximal end 5. In the rectangular design, as shown in FIG. 2, there is a walled first 6 and second 7 longitudinal sides, a base 8, a hollow top surface 9 and a protrusion 10 placed at the distal end of either one or both of the longitudinal walls 6 and 7.

In the cylindrical design, a hollow top opening 9a extends from the distal end 4a to the closed walled proximal end 5a. The sides along the length of the cylindrical, ovoid or similarly shaped needle holder is still referred to as the walled first and second longitudinal sides 6a or 7a even if one side is continuously connected to the other side, unlike in a rectangle where there is a distinct break between the longitudinal sides and the base. The protrusion 10a is placed at the distal end of either one or both of the longitudinal sides, 6a and 7a.

The protrusion 10 or 10a extends radially outward from the outer surface of the walls along the longitudinal sides 6 or 6a and 7 or 7a and is preferably slanted, with the thicker end towards the proximal end and is also preferably made of the same polymeric material as the body of the needle holder. The protrusion 10 or 10a functions both as a stopping device and an engagement device between the needle sleeve and the needle holder.

In the rectangular design, the walls along the longitudinal sides 6 and 7 have an overhang 11 bordering the entire length of the longitudinal walls which extends internally, that is, inwardly towards the interior of the needle holder. For the cylindrical design, the curvature 21 bordering the hollow top surface or opening 9a functions as the overhang 11. The wall that laterally borders the closed wall proximal end 5 or 5a may extend slightly pass the longitudinal walls 6 or 6a and 7 or 7a to cause a protruding fence 12 which can be either on one side or on both sides of the closed wall proximal end 5 or 5a as shown in FIG. 2. On one embodiment of a needle holder of this invention as shown in FIGS. 2 and 2A, midway from the inner wall 13 of the closed proximal end 5 or 5a is a needle handle for holding the needle. The needle handle is a solid protruding body 14, preferably cylindrical in shape through which a sharp metallic or hard polymeric needle 15 is permanently attached as shown in FIGS. 2 and 2A. The needle handle 14 may have a pair of horizontally oriented wing-like structure 16 projecting from the opposite lateral sides of the needle handle to provide greater firmness and stability to the needle. Alternate designs for the wing like structure are shown in FIGS. 2 and 2A. The wing-like projections 16 preferably extends to the inner walls 17 of the longitudinal walls 6 or 6a and 7 or 7a as shown in FIGS. 2 and 2A. The distal end of the needle protrudes from the needle holder 1. The needle has a hollow interior, lumen 18, and could vary in sizes and gauges. The proximal end of the needle is connected to a two ended connector 19. The connector is preferably made of the same polymeric material as the needle holder. The connector 19 has a hollow conical interior, a cone tapered shaped cavity, converging at one end with the proximal end of the hollow needle 15 so as to communicate with the lumen 18 of the needle, through which materials, preferably liquids or suspensions, may be introduced. The other end of the connector, one not connected to the needle, preferably has a luer lock tip 20.

Figure 2C:
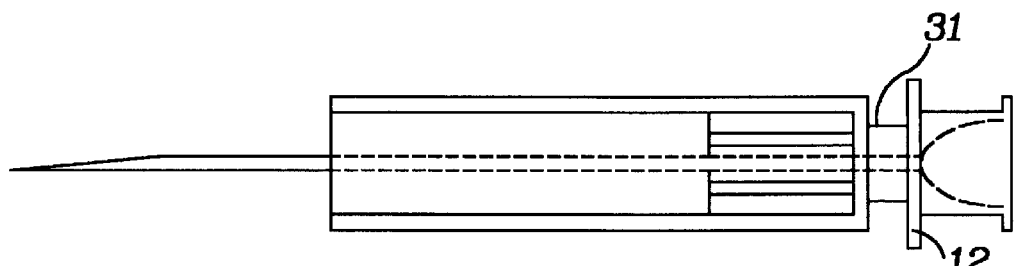
FIG. 2C is a top view of the needle holder of FIG. 2B.

In another embodiment of a needle holder of this invention as shown in FIGS. 2B and 2C, the needle holder further comprise of a recessed cylindrical extension 31 between a first 5a and a second 5b closed walled proximal end and a cut out area 32 from the top of the first closed walled proximal end of the needle holder 1 for accommodating an interlocking member 3 that clamps rather than slips into the needle holder. The width of the recessed cylindrical extension 31 of the needle holder 1 varies, it may be as narrow as a wire if for example, the clamping means of the interlocking member is shaped like a ring or it may be wider to match the width of the clamping means. The depth of the recessed cylindrical extension 31 matches the thickness of the clamping means of the interlocking member 3 while the depth of the cut out area 32 on the first close walled proximal end 5a matches the thickness of the interlocking member 3 such that the outer walls of the needle holder, the interlocking member when pressed into the hollow top surface 9 and that of the connector 19, preferably align when the interlocking member 3 is clamped into the needle holder 1. Although a cylindrical needle holder with a recessed cylindrical extension is shown in FIG. 2B, this same embodiment, as in the first embodiment described above, can also be rectangular, ovoid or similarly shaped.

Figure 3:
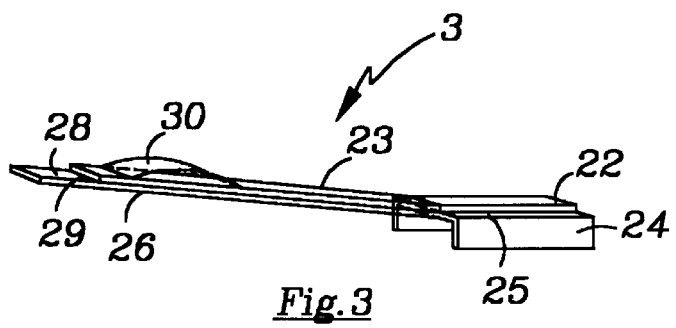
FIG. 3 is a perspective view of one embodiment of an interlocking member.

One embodiment of the interlocking member slips into the needle holder while another embodiment clamps into the needle holder. The interlocking member 3 as shown in FIG. 3 slips into the hollow surface 9 of the needle holder 1 and is held inside the hollow top surface of the needle holder by the overhang 11 along the longitudinal walls 6 and 7 of the rectangular needle holder or by the curvature 21 for the cylindrical, ovoid or similarly shaped needle holder. The proximal end 22 of the interlocking member 3 is preferably planar for the rectangular needle holder. Connected along the longitudinal edges 23 at the proximal end of the interlocking member is a downward step-legged projection 24 that stands on the base 8 of the needle holder 1 to support the interlocking member 3. For needle holders with wing-like projections 16, the step-legged projection 24 is shorter because it stands on top of the wing-like projection 16 rather than extending all the way to the base 8 of the needle holder. The step-legged projection fits underneath the overhang 11. The step portion 25 of the step-legged projection 24 and the overhang 11 are shaped to match each other and are of the same dimensions to allow a good fit. For cylindrical, ovoid, or similarly shaped needle holders, the entire outer surface of the interlocking member is preferably curved in such a direction that when the interlocking member slips into the curvature 21, the interlocking member covers the top opening or top surface 9a of the needle holder to result in a cylindrically shaped outer surface. The distal end of the interlocking member 3 preferably extends upward at an angle. This distal angular end is hereinafter referred to as the angular end 26. The interlocking member 3 is of such width that its longitudinal edges 23 just freely rub on the longitudinal inside tip 27 of the needle holder 1, allowing unimpeded up and down motion of the angular end 26. At the distal portion of the angular end 26 is a stepped recess which look like a fore and middle finger projection, hence will be referred to as finger hook 28. The finger hook has a notch 29. Before the finger hook 28, for the planar interlocking member, there is preferably, a slightly elevated hump 30 to allow a tighter engagement between the interlocking member 3 and the needle sleeve 2.

The interlocking member 3, as the needle holder 1, may be made of solid material or it may have a hollow interior. It can be made of metal, hard rubber compound, but is preferably made of the same preferred polymeric material used for the needle holder 1 but is of a kind that is non-brittle, durable and resilient with memory. With memory means the material will return to its original configuration when the restraining means which keeps the material stationary at a strained position, is released.

Figure 3A:
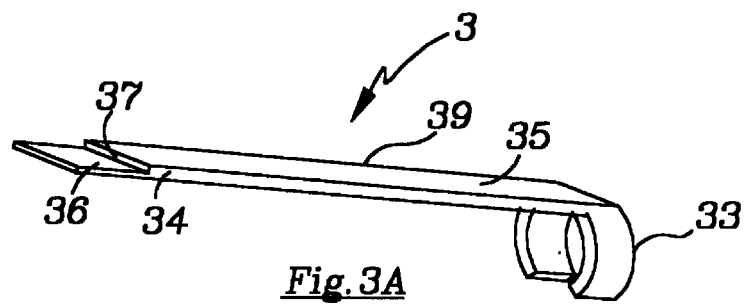
FIG. 3A is a perspective view of another embodiment of an interlocking member.

The interlocking member 3 as shown in FIG. 3A clamps or snaps into the recessed cylindrical extension 31 shown in FIGS. 2A and 2B of one embodiment of the needle holder 1. At the proximal end of the interlocking member 3 is a clamp 33 shaped like a letter "C" facing downwards as shown by FIG. 3A and hence will be referred to as the C-clamp 33. The C-clamp 33 clamps or snaps into the outer surface of the cylindrical extension 31 which is preferably recessed compared to the main outer surface of the needle holder 1, as shown in FIGS. 2B and 2C, to accommodate the C-clamp. For the rectangular needle holder, the interlocking member 3 is planar or flat as shown in FIG. 3. In the cylindrical, ovoid or similarly shaped needle holder, the interlocking member is preferably curved such that when the interlocking member 3 is clamped to the needle holder, positioned over the cut out area 32, the interlocking member 3 covers the top opening of the needle holder as shown in FIG. 1A to result into a cylindrical outer surface. The interlocking member 3 extends upwardly at an angle. The distal angular end 34 is hereinafter referred to as angular end 34 and the proximal end connected to the C-clamp 33 will be referred to as proximal end 35. The angular end 34 has the same width as the proximal end 35. The interlocking member 3 is of such width that its longitudinal edges 39 just freely rub on the longitudinal inside tip of the needle holder 27 or 27a, allowing unimpeded up and down motion of the interlocking member. At the distal portion of the angular end 34 is a stepped recess which look like a fore and middle finger projection, hence will be referred to as finger hook 36. The finger hook has a notch 37. Before the finger hook 36, for the planar interlocking member, there is preferably, a slightly elevated hump 38 to allow a tighter engagement between the interlocking member 3 and the needle sleeve 2.

The needle sleeve 2 is shaped to conform with the outer contour and surface of the needle holder 1. For ease of handling, the needle sleeve is preferably shaped like a hollow rectangular box, as shown in FIG. 4 or a hollow cylindrical or ovoid tube for the cylindrical or ovoid needle holder as shown in FIG. 4A. The needle sleeve has an open proximal 40 and distal 41 lateral ends to allow the needle sleeve 2 to slide over the needle holder 1 in a telescopic manner relative to the needle holder. The closed sides of the rectangular needle sleeve are the longitudinal side walls 42 and 43 and the top and bottom surfaces 44 and 45. The top surface 44 of the rectangular needle sleeve has a cutout area 46 on the proximal end 40, preferably rectangular in shape as shown in FIG. 4. The cutout area has three sides, two horizontal sides 47 and 48 and a frontal side 49. All three sides may be blunt ended but it is preferable for the frontal side 49 to have a slant edge as shown in FIG. 4. The cut out area leaves a horizontal overhang 50. For the rectangular needle sleeve, the overhang 50 rests over the overhang 11 of the needle holder 1. The overhang 11 functions like a track over which the sleeve traverses to and from.

For the cylindrical, ovoid or similarly shaped needle sleeve as shown in FIG. 4A, the cut out area 46a from the proximal end 40a of the needle sleeve is also preferably rectangular in shape and is of the same width as the hollow top surface opening 9a of the needle holder. A curved surface 52 is left after cutting out area 46a which functions like the overhang 50 and rests over the curvature 21 on the main body of the needle holder. The curvature 21 functions as a tract through which the needle sleeve traverses to and from. For the cylindrical or other similarly shaped design such as an ovoid, the only difference from that of the rectangular shaped needle sleeve is the absence of corners to distinguish the sides, that is, there is no distinct break differentiating one side from the other.

At a calculated or measured distance, starting approximately a third of the full length of the needle sleeve 2 from the proximal end 40 or 40a, are grooves 51 along the inner surface of the longitudinal walls 42 or 42a and 43 or 43a as shown in FIG. 4. These grooves engage with the protrusion 10 or 10a and function as a track (shown in broken line) through which the protrusion 10 or 10a can traverse to and from horizontally as shown in FIG. 5. The outer surface of the longitudinal walls 42 or 42a and 43 or 43a of the needle sleeve may be smooth or gridded. However, it is preferable to grid the outer sides of the walls to provide a better grip for the user. The needle sleeve, as the needle holder, can also be made of metal, glass hard rubber compound or plastic polymeric material but is preferably made of the same polymeric material as those used for the needle holder and interlocking member.

When the sliding needle sleeve 2 is slid over the top surface of the needle holder 1 from a position covering the needle holder as shown in FIG. 6, to a direction towards the tip of the needle 15, the leafspring action of the angular end 26 or 34 allows the finger hook 28 or 36 to rest on the inside wall of the top surface 44 or 44a of the sliding needle sleeve and the notch 29 or 37 to rest on its frontal side 49 as shown in FIG. 1. At this position, the entire needle is shielded and the sleeve is temporarily locked. Leafspring effect is the counter effect produced when the upward angular distal 26 or 34 end of the interlock member is pressed downward while the proximal end 22 or 35 is kept stationary in one position. The needle assembly with the needle sleeve 2 in this forward position, shielding the needle 15, is temporarily locked in this position by the finger hook 28 or 36 abutting on the frontal side 49 of the cutout area afforded by its leafspring effect. The finger hook 28 or 36 protrudes over the top surface 44 thereby preventing the needle sleeve 2 from moving away from the direction of the needle, as shown in FIG. 1. On the other hand, the forward motion of the needle sleeve 2 towards the direction of the needle is checked when the protrusion 10 or 10a abuts at the end 53 of the grooves 51 as shown in FIG. 5. The grooves 51 prevent the needle sleeve 2 from disengaging with the protrusion 10 or 10a of the needle holder.

The procedure for exposing the distal tip of the needle 15 from a position where the needle sleeve 2 shields the entire needle body is accomplished by pressing on the top surface of the finger hook 28 or 36 downward or if there is a hump 30 or 38, on the hump, towards the hollow top surface 9 or 9a of the needle holder, to release its engagement from the frontal side 49. Once the finger hook 28 or 36 no longer abuts on the frontal side 49, the needle sleeve can be manually moved rearward or slid rearward in a direction away from the needle, thereby exposing its distal end as shown in FIG. 6. At this position, the needle is free for usage for any purpose such as injection, infusion, pricking and the like. The needle sleeve 2 is collectively kept from moving forward or rearward during its use by the slightly flaired edge 54 at the outside junction between the longitudinal walls 6 and 7 and the fence 12, and the hump 30 or 38 touching on the inner surface 55 of the needle sleeve, providing resistance to unassisted movement. Further, since the inside surface dimensions of the needle sleeve is barely larger than the outer surface dimensions of the needle holder, only enough to allow it to slide over the needle holder, additional frictional resistance is provided. The protruding fence 12 on one or both sides of the closed walled proximal end 5 or 5b of the needle holder also stops any further rearward motion of the needle sleeve 2. After use, the needle sleeve 2 is merely pushed forward to a position wherein the finger hook 28 or 36 reengages automatically with the frontal side 49 because of the angular design and leafspring effect of the distal portion of the interlock member. This process allows one to manually slide with ease, the needle sleeve 2, forward and rearward in relation to the needle holder 1, to cover and uncover the sharp distal end of the needle 15 without the use of a spring device and complex mechanisms.

For packaging, shipping or when discarding the needle assembly after use, it is preferable to incorporate a capping component 56 for covering the distal and the proximal end of the needle assembly to further prevent accidental puncture or scratching with the tip of the needle. The cap can be made of metal, glass or hard rubber compound but is preferably made the same polymeric material as those used for the other components of the needle assembly. As shown in FIG. 1A, it is sufficient to have only one cap covering the open distal end of the needle assembly if the entire assembly, for example, will be packaged inside a pouch or container. If only one cap is used, the cap 56 extends preferably from the distal tip of the needle sleeve to a position in front of the finger hook 28 or 36 which protrudes over the needle sleeve 2 when the needle assembly is stored or discarded as shown in FIG. 1A. The inner wall of the cap 56 is thicker at its distal end than at its proximal end to cause the cap to receive and fit snugly into the needle assembly thereby preventing the cap 56 from unassisted slippage as shown in FIG. 7.

Due to the simplicity in design of the needle assembly and the availability of needles and suitable plastic materials at rather reasonable prices, this device can be made available as a disposable product for one time or limited time usage.

While the embodiments of the present invention have been described, it should be understood that various changes, adaptations, and modifications may be made therein without departing from the spirit of the invention and the scope of the claims.

What is claimed is:

1. A needle assembly for use with a fluid delivery device, comprising:

a needle holder having a closed walled proximal end, an open distal end, a walled first and second longitudinal side, a base, a hollow top surface, a needle handle protruding from the inner wall of the closed walled proximal end, a hollow needle, and a two ended hollow connector mounted to the hollow needle at one end;

a sliding needle sleeve for surrounding the needle holder, the sleeve slidably movable relative to the needle holder in the direction of the length of the needle from a first position in which the needle projects outside of the needle sleeve to a second position in which the needle is within the needle sleeve;

means for engaging the needle holder with the needle sleeve;

means for interlocking the needle sleeve with the needle holder; and, means for stopping the rearward and forward motion of the needle sleeve relative to the needle holder.

2. The needle assembly of claim 1 wherein the needle assembly is made of material selected from the group consisting of glass, metal, hard rubber compound and plastic polymeric material.

3. The needle assembly of claim 2 wherein the polymeric material is selected from the group consisting of polyvinyl chloride, polyvinylacetate, polyethylene, polypropylene, nylon, polycarbon, polyurethane, ethylene vinyl acetate, polysulfone and combinations of any of these formulations.

4. The needle assembly of claim 1 wherein the first and second longitudinal walls of the needle holder have overhangs bordering the entire length of the walls and directed inwards for receiving the interlocking means.

5. The needle assembly of claim 1 wherein the hollow needle has a lumen in direct communication with the hollow connector, the hollow connector having a conical interior cavity tapering into the lumen of the needle.

6. The needle assembly of claim 1 wherein the other end of the hollow connector not connected to the needle has a luer lock tip.

7. The needle assembly of claim 1 wherein the needle handle is cylindrical having a pair of horizontally oriented wing-like structure.

8. The needle assembly of claim 1 wherein the needle sleeve has a gridded area on the outer surface.

9. The needle assembly of claim 1 further comprising of a cap means for closing an end of the needle assembly.

10. The needle assembly of claim 1 wherein the means for interlocking the needle sleeve with the needle holder is an interlocking member comprising a proximal end, an angular distal end, a downward step-legged projection on the proximal end, a step portion of the step-legged projection abutting on the overhang along the first and second longitudinal walls of the needle holder when introduced therethrough, and a finger hook on the distal angular end for engagement and release.

11. The needle assembly of claim 1 wherein the needle assembly is disposable.

12. The needle assembly of claim 1 further comprising a second closed walled proximal end, a recessed cylindrical extension between the closed walled proximal end and the second closed walled proximal end, and a cut out area from the top of the closed walled proximal end.

13. The needle assembly of claim 12 wherein the means for interlocking the needle sleeve with the needle holder is an interlocking member comprising a proximal end, an angular distal end, a clamp on the proximal end, and a finger hook on the distal angular end for engagement and release.

14. A needle assembly for use with a fluid delivery device, comprising:

a needle holder having a walled first and second longitudinal side, an overhang directed internally bordering along the entire length of the first and second longitudinal walls, a protrusion on the distal outer surface of the longitudinal walls, an open distal end, a closed walled proximal end, the closed proximal end extending slightly beyond the longitudinal walls, a base, a hollow top surface, a needle handle protruding midway from the inner wall of the closed walled proximal end, a hollow needle, and a two ended hollow connector mounted to the hollow needle at one end;

an interlocking member having a proximal end and an angular distal end, the proximal end having a downward step-legged projection for support, a step portion on the longitudinal sides of the step-legged projection abutting on the overhang along the first and second longitudinal walls of the needle holder when introduced therethrough, a hump between the proximal and the angular distal end, and a finger hook on the distal angular end for engagement and release;

a sliding needle sleeve for surrounding the needle holder, the needle sleeve having an open proximal and distal end to receive the needle holder therethrough, closed walled longitudinal, bottom and top surfaces, a groove along the inner surface of the longitudinal wall for engaging with the protrusion on the outer surface of the needle holder thereby permitting traversal of the protrusion along the groove, a cut out area on the top surface for engaging with the finger hook of the interlocking member thereby temporarily locking the needle sleeve to a position shielding the distal tip of the hollow needle; and means for controlling the position of the needle sleeve relative to the needle holder thereby shielding or exposing the hollow needle as desired.

15. A needle assembly for use with a fluid delivery device, comprising:

a needle holder having a walled first and second longitudinal side, an overhang directed internally bordering along the entire length of the first and second longitudinal walls, a protrusion on the distal outer surface of the longitudinal walls, an open distal end, a first and second closed walled proximal end, the second closed proximal end having an extension beyond the longitudinal walls, a recessed extension between the first and second closed walled proximal end, a cut out area from the top of the first closed walled proximal end of the needle holder, a base, a hollow top surface, a needle handle protruding midway from the inner wall of the closed walled proximal end, a hollow needle, and a two ended hollow connector mounted to the hollow needle at one end;

an interlocking member having a proximal end and an angular distal end, a hump between the proximal and the angular distal end, a clamp at the proximal end for attachment into the recessed cylindrical extension of the needle holder, and a finger hook on the distal angular end for engagement and release;

a sliding needle sleeve for surrounding the needle holder, the needle sleeve having an open proximal and distal end to receive the needle holder therethrough, closed walled longitudinal, bottom and top surfaces, a groove along the inner surface of the longitudinal wall for engaging with the protrusion on the outer surface of the needle holder thereby permitting traversal of the protrusion along the groove, a cut out area on the top surface for engaging with the finger hook of the interlocking member thereby temporarily locking the needle sleeve to a position shielding the distal tip of the hollow needle; and means for controlling the position of the needle sleeve relative to the needle holder thereby shielding or exposing the hollow needle as desired.

* * * * *